United States Patent [19]

Pasedach et al.

[11] 4,173,588

[45] Nov. 6, 1979

[54] MANUFACTURE OF 2-METHYL-2-HEPTEN-6-ONE

[75] Inventors: Heinrich Pasedach, Ludwigshafen; Rudolf Mohr, Lampertheim; Axel Nissen, Leimen, all of Fed. Rep. of Germany

[73] Assignee: BASF Aktiengesellschaft, Fed. Rep. of Germany

[21] Appl. No.: 848,211

[22] Filed: Nov. 3, 1977

[30] Foreign Application Priority Data

Nov. 20, 1976 [DE] Fed. Rep. of Germany ....... 2652863
Jul. 2, 1977 [DE] Fed. Rep. of Germany ....... 2729975

[51] Int. Cl.$^2$ ............................................. C07C 45/18
[52] U.S. Cl. .................................................. 260/595
[58] Field of Search ......................................... 260/595

[56] References Cited

U.S. PATENT DOCUMENTS

| | | | |
|---|---|---|---|
| 2,795,617 | 6/1957 | Kimel et al. | 260/595 |
| 3,023,246 | 2/1962 | Pasedach et al. | 260/595 |
| 3,101,375 | 8/1963 | Crocker | 260/595 |
| 3,238,260 | 3/1966 | Pasedach et al. | 260/595 |
| 3,975,446 | 8/1976 | Kitogaki et al. | 260/595 |

*Primary Examiner*—James H. Reamer
*Attorney, Agent, or Firm*—Keil & Witherspoon

[57] ABSTRACT

An improved process for the manufacture of 2-methyl-2-hepten-6-one by reacting an alkyl acetoacetate with 2-methyl-3-buten-2-ol in the presence of an organic aluminum compound such as aluminum trialcoholate, aluminum triacetoacetate, aluminum alkylacetoacetate or aluminum triaryloxylate. 2-Methyl-2-hepten-6-one is an intermediate for the manufacture of vitamins.

8 Claims, No Drawings

MANUFACTURE OF 2-METHYL-2-HEPTEN-6-ONE

The present invention relates to an improved process for the manufacture of 2-methyl-2-hepten-6-one by reacting an alkyl acetoacetate with 2-methyl-3-buten-2-ol at an elevated temperature in the presence of an organic aluminum compound such as aluminum trialcoholate, aluminum triacetoacetate, aluminum alkyl acetoacetate or aluminum triaryloxylate.

Apart from the improvements according to the present invention, this process has been disclosed by Teisseire et al. "Recherches," June 1956, page 31. The yield is only about 56%, which is entirely inadequate for industrial syntheses. If, instead of an alkyl acetoacetate, diketene is reacted with 2-methyl-3-buten-2-ol in the presence of aluminum triisopropylate, 2-methyl-2-hepten-6-one is obtained in a yield of 83% (cf. "Advances in Organic Chemistry," Volume II, 1960, page 246). It is to be deduced from the last-mentioned publication that for the manufacture of 2-methyl-2-hepten-6-one, diketene is to be preferred over an alkyl acetoacetate as the starting material. This is undoubtedly true on a laboratory scale, but unacceptable for the industrial manufacture of methylheptenone. For safety reasons alone, the instability of diketene demands the use of expensive apparatus. In addition, in order to achieve high yields and smooth operation of the plant, measures are required which substantially cancel out the advantage of the good yield. Further, German Pat. No. 1,068,696 discloses the preparation of 2-methyl-2-hepten-6-one by passing 2-methyl-3-buten-2-ol into a reaction mixture which has been preheated to 160°–250° C. and comprises an alkyl acetoacetate, a mixture of an alkyl acetoacetate and an inert solvent, or a mixture of 2-methyl-3-buten-2-ol, an alkyl acetoacetate and a solvent. However, this process also gives yields of only from 63 to 66% of theory, based on alkyl acetoacetate converted.

It is an object of the present invention to provide a more economical method than hitherto for the manufacture of methylheptenone from alkyl acetoacetates and 2-methyl-3-buten-2-ol.

We have found, surprisingly, that this object is achieved and that 2-methyl-2-hepten-6-one is obtained in very high yields by reacting 2-methyl-3-buten-2-ol with alkyl acetoacetates at an elevated temperature and in the presence of an organic aluminum compound, if the methylbutenol and the alkyl acetoacetate are reacted at from 140° to 180° C., using a molar ratio of from 0.8:1 to 2.0:1, preferably from 1:1 to 1.5:1, under such conditions that any period(s) for which the concentration of alkyl acetoacetate in the reaction mixture exceeds 15% by weight are not more than 2 hours and preferably not more than 1 hour in all. It is particularly advantageous if the concentration of alkyl acetoacetate in the reaction mixture never exceeds 5% by weight.

In practice, the conditions required according to the invention may be achieved in a simple manner by, for example, introducing, into a reaction vessel possessing a fractionating column, a solution of the aluminum compound in the alkyl acetoacetate, in a mixture of the alkyl acetoacetate and small amounts of methylbutenol, in a high-boiling inert solvent, e.g., tetralin or dimethylformamide, or in a high-boiling weak base, e.g., quinoline or dimethylaniline, or in a small amount of the reaction product 2-methyl-2-hepten-6-one, and introducing methylbutenol and the alkyl acetoacetate into this solution at the reaction temperature, at the rate at which the reaction progresses, in a molar ratio such that within 2 hours, preferably within 1 hour, a molar excess of methylbutenol is present in the reaction mixture, whilst ensuring that the alcohol formed in the reaction distills off at the top of the fractionating column, without this alcohol containing any significant amount of methylbutenol.

The progress of the reaction may be followed by measuring the carbon dioxide evolved and/or the amount of alkanol eliminated from the alkyl acetoacetate. The concentration of the alkyl acetoacetate in the reaction mixture can be determined by analysis by gas chromatography.

On the other hand, simply introducing the alkyl acetoacetate into excess methylbutenol, containing the aluminum compound, at the reaction temperature is not possible since the boiling point of 2-methyl-3-buten-2-ol is as low as 98° C., whilst the reaction only starts above 140° C.

In a particularly advantageous embodiment of the process according to the invention, the methylbutenol and the alkyl acetoacetate are introduced, at from 140° to 180° C., in a molar ratio of from 1.1:1 to 1.5:1, into a solution of the aluminum compound in 2-methyl-2-hepten-6-one, at a rate such that the concentration of alkyl acetoacetate in the reaction mixture is never more than 15% by weight and preferably never more than 5% by weight.

Under the reaction conditions according to the invention, the reaction is carried out in such a way that virtually no methylbutenol acetoacetate is detectable in the mixture; this is essential if the high yields according to the invention are to be achieved.

In principle, the reaction can be carried out with any alkyl acetoacetate, but the methyl ester and ethyl ester are preferred both for economic and for technological reasons, since their alcohols boil lower than 2-methyl-3-buten-2-ol (boiling point=98° C.) and can therefore be removed continuously from the reaction mixture by fractional distillation.

The amount of methylbutenol to be employed is preferably at least 1.1 moles per mole of alkyl acetoacetate. It depends on the separating capacity of the fractionating column. The better is the latter, the lower are the amounts of methylbutenol which are lost in the course of distilling off the alcohol. In general, from about 1.2 to 1.5 moles of methylbutenol are required per mole of alkyl acetoacetate.

Suitable organic aluminum compounds for the process according to the invention are those of the general formula

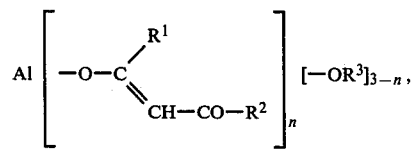

where $R^1$ and $R^2$ are alkyl or alkoxy of 1 to 4 carbon atoms, preferably methyl or ethyl, $R^3$ is alkyl of 1 to 4 carbon atoms and n is 0, 1, 2 or 3. Accordingly, these compounds are lower aluminum trialcoholates, e.g., aluminum trimethylate, aluminum triethylate, aluminum triisopropylate and aluminum tri-sec.-butylate, and compounds which are formed, with elimination of alcohol, on reacting the said aluminum trialcoholates with stoichiometric amounts of an acetylacetonate, alkyl acetoacetate or alkyl malonate. Examples are aluminum triacetoacetate, aluminum triacetylacetonate, aluminum monoacetoacetate diethylate, aluminum diacetoacetate monoethylate, aluminum monoacetoacetate diisopropylate and aluminum diacetoacetate monoisopropylate. The use of the aluminum trialcoholates, especially of aluminum triisopropylate, is particularly preferred.

Further, we have found that this process gives a particularly pure 2-methyl-2-hepten-6-one if the organic aluminum compound employed is an aluminum triaryloxylate, which compounds have hitherto not been employed for such reactions.

For the purposes of the invention, aluminum triaryloxylate means an aluminum salt of an aromatic hydroxylic compound, e.g. aluminum triphenolate, the aluminum tricresolates, the aluminum trixylenolates and the aluminum trinaphtholates, the aryl radicals of which may or may not be substituted by lower alkyl or alkoxy, i.e., alkylor alkoxy of 1 to 4 carbon atoms, hydroxyl or phenyl. It is particularly advantageous to use aluminum triphenolate, which is relatively easily accessible.

The amount of the aluminum compound is generally so chosen that the concentration in the reaction mixture does not fall below 0.05% by weight of Al and does not exceed 6% by weight of Al at the start of the reaction. In general, from 1 to 5% by weight, based on alkyl acetoacetate to be converted, of the aluminum compound are required. In the case of aluminum triisopropylate, the preferred compound, the amounts required are, for example, from about 1 to 3% by weight of Al, based on alkyl acetoacetate to be converted, are required. The reaction may be carried out continuously or batchwise and is advantageously carried out under atmospheric pressure. However, the use of superatmospheric pressure, of from about 1 to 10 atmospheres gauge, often offers advantages when using industrial equipment, since it provides a convenient method of maintaining a higher concentration of the relatively low-boiling methylbutenol in the reaction mixture. At the same time, better separation of methanol and methylbutenol in the fractionating column is achieved; when working at atmospheric pressure, the carbon dioxide liberated makes this separation difficult.

The amount of methylbutenol to be employed can be reduced substantially by working under superatmospheric pressure. Furthermore, such pressures, of from 1 to 10 atmospheres gauge, allow the reaction temperature to be raised to 170°-180° C. The batch time is substantially reduced and hence the capacity of the plant is substantially increased. At the shorter reaction times achieved, the activity of the aluminum alcoholate suffers less.

The reaction mixtures are advantageously worked up by distillation; first, the methylbutenol and low-boiling by-products are separated off and thereafter the methylheptenone is subjected to fractional distillation. Any desired degree of purity is achievable in this way. If the methylheptenone obtained is to be employed as a solvent for the reaction according to the invention, prior purification by distillation is not necessary. Instead, the crude methylheptenone, containing at least 85% by weight of the said compound, can be employed. The residue obtained contains the aluminum compound plus any high-boiling solvent. This residue may be used for subsequent reaction batches.

Using the process according to the invention, 2-methyl-2-hepten-6-one is obtained in the unexpextedly high yields of more than 90% of theory. Accordingly, the measures according to the invention prevent the formation of resinified products, usually encountered in this reaction, the formation of substantial amounts of acetone and isoprene, and the formation of prenyl acetoacetate, which can only be converted incompletely to methylheptenone.

The use, according to the invention, of aluminum salts of aromatic hydroxylic compounds instead of the conventionally used aluminum salts of aliphatic hydroxylic compounds is very advantageous, since it avoids the formation, which occurs in the process using conventional aluminum salts, of up to 3% of an impurity in methylheptenone, which has not hitherto been investigated but is difficult to remove. As a result of this impurity not being formed, working up the reaction mixture by distillation is greatly simplified, and this is exceptionally important, since methylheptenone is generally marketed as very pure material, such as is required for further conversion to scents or vitamins.

2-Methyl-2-hepten-6-one is a valuable intermediate for the manufacture of scents and vitamins, e.g., vitamin A.

EXAMPLE 1

In a reaction vessel with an attached distillation column, 10 g of aluminum triisopropylate are dissolved in 50 g of 2-methyl-2-hepten-6-one, the solution is heated at from 148° to 151° C., and in the course of 12 hours 464 g (4 moles) of methyl acetoacetate and 430 g (5 moles) of 2-methyl-3-buten-2-ol are introduced simultaneously and in a constant feed ratio. At the same time, the methanol formed is distilled off.

After the evolution of methanol and $CO_2$ has ceased, the reaction mixture is worked up by distillation. 99 g of unconverted 2-methyl-3-buten-2-ol and 497 g of 2-methyl-2-hepten-6-one of boiling point 78° C./30 mm Hg are obtained. The yield of methylheptenone is 447 g=92% of theory, based on methylbutenol converted, or 88.7% of theory, based on alkylacetoacetate employed.

During the reaction, the composition of the reaction mixture, in % by weight, is as shown in the Table (analysis by gas chromatography: OV17 column material, temperature 100° C., followed by 130° C.).

| After hours reaction time | 2-Methyl-3-buten-2-ol, % | Methyl acetoacetate % | 2-Methyl-2-hepten-6-one, % | Methylbutenol acetoacetate | Prenyl acetoacetate |
|---|---|---|---|---|---|
| 1 | 10.6 | 2.4 | 86.4 | — | — |
| 3 | 11.9 | 1.0 | 83.1 | — | — |
| 6 | 14.4 | 2.6 | 82.9 | — | — |
| 9 | 11.4 | 1.0 | 87.5 | — | — |
| 12 | 10.2 | 0.8 | 89.2 | — | — |
| end | 11.1 | 0 | 88.5 | — | — |

EXAMPLE 2

10 g of aluminum triisopropylate and 50 g (0.43 mole) of methyl acetoacetate are heated at 147°–153° C. in the reaction apparatus described in Example 1, and 414 g (3.57 moles) of methyl acetoacetate and 430 g (5 moles) of 2-methylbuten-3-ol-2 are introduced simultaneously in the course of 16 hours, in a constant feed ratio.

| After hours reaction time | 2-Methyl-3-buten-2-ol, % | Methyl acetoacetate % | 2-Methyl-2-hepten-6-one, % | Methylbutenol acetoacetate | Prenyl acetoacetate |
|---|---|---|---|---|---|
| 2 | 11.1 | 13.2 | 75.7 | — | — |
| 4 | 7.2 | 5.7 | 86.1 | — | — |
| 6 | 8.2 | 4.3 | 87.5 | — | — |
| 12 | 10.3 | 3.5 | 86.2 | — | — |
| 16 | 9.1 | 0 | 90.9 | — | — |

The formation of methanol has ceased 1 hour after the end of the addition, and after from about 1 to 2 hours, again from the end of the addition, the evolution of carbon dioxide also ceases.

On working up the mixture by distillation when the reaction has ceased, 90 g of unconverted 2-methyl-3-buten-2-ol, 442 g of 2-methyl-2-hepten-6-one, 17 g of acetone and 22 g of isoprene are obtained.

The yield of methylheptenone is 88.6% of theory, based on methylbutenol converted, and 87.7%, based on alkyl acetoacetate employed.

During the reaction, the composition of the reaction mixture, in % by weight, is as shown in the Table (analysis by gas chromatography: OV17 column material, temperature 100° C., followed by 130° C.).

| After hours reaction time | 2-Methyl-3-buten-2-ol, % | Methyl acetoacetate % | 2-Methyl-2-hepten-6-one, % | Methylbutenol acetoacetate | Prenyl acetoacetate |
|---|---|---|---|---|---|
| 2 | 11.1 | 7.8 | 81.1 | — | — |
| 4 | 8.2 | 4.9 | 86.9 | — | — |
| 7 | 6.2 | 0.3 | 93.5 | — | — |
| 11 | 12.5 | 3.0 | 84.5 | — | — |
| 14 | 13.6 | 5.2 | 81.2 | — | — |
| end | 10.0 | 0 | 90.0 | — | — |

EXAMPLE 3

5 g of aluminum triisopropylate, 100 g (0.86 mole) of methyl acetoacetate and 28 g (0.33 mole) of methylbutenol are heated at 150°–154° C. in the reaction apparatus described in Example 1, and 47 g (0.54 mole) of methylbutenol are added to the solution obtained, in the course of 2 hours. The methanol formed is distilled off. A mixture of 364 g (3.14 moles) of methyl acetoacetate and 355 g (4.12 moles) of methylutenol is then introduced in the course of 14 hours.

On working up the reaction mixture by distillation when reaction has ceased, 444 g of 2-methyl-2-hepten-6-one, 88 g of unconverted 2-methyl-3-buten-2-ol, and 15 g of acetone and 4 g of isoprene as by-products are obtained. The yield of methylheptenone is 88.8% of theory, based on alkyl acetoacetate employed.

During the reaction, the composition of the reaction mixture, in % by weight, is as shown in the Table (analysis by gas chromatography: OV17 column material, temperature 100° C., followed by 130° C.).

EXAMPLE 4

7.5 g of aluminum triisopropylate and 50 g of a reaction product which contains 42 g of 2-methyl-2-hepten-6-one and 5 g of 2-methyl-3-buten-2-ol are heated at 150° C. in the reaction apparatus described in Example 1, and a mixture of 464 g of methyl acetoacetate and 430 g of 2-methyl-3-buten-2-ol is introduced in the course of 18 hours. On working up the mixture by distillation when the reaction has ceased, 490 g of 2-methyl-2-hepten-6-one, 95 g of unconverted 2-methyl-3-buten-2-ol, 13 g of acetone and 4 g of isoprene are obtained. The yield (448 g) is 89% of theory, based on methyl acetoacetate employed, and 90.1%, based on methylbutenol converted.

During the reaction, the composition of the reaction mixture, in % by weight, is as shown in the Table (analysis by gas chromatography: OV17 column material, temperature 100° C., followed by 130° C.).

| After hours reaction time | 2-Methyl-3-buten-2-ol, % | Methyl acetoacetate % | 2-Methyl-2-hepten-6-one, % | Methylbutenol acetoacetate | Prenyl acetoacetate |
|---|---|---|---|---|---|
| 2 | 9.8 | 5.7 | 84.5 | — | — |
| 4 | 8.7 | 4.3 | 87.0 | — | — |
| 7 | 11.1 | 3.7 | 85.2 | — | — |
| 10 | 7.9 | 2.9 | 89.2 | — | — |
| 13 | 8.3 | 2.7 | 89.0 | — | — |
| 16 | 9.2 | 2.3 | 88.5 | — | — |
| 18 | 8.7 | 0 | 91.3 | — | — |

EXAMPLE 5

A mixture of 15 g of aluminum triphenolate, 78 g (0.67 mole) of methyl acetoacetate and 72 g (0.84 mole) of 2-methyl-3-buten-2-ol is heated at 145° C. in a reaction vessel connected to a distillation column. In the course of 9.5 hours, a mixture of 386 g (3.33 moles) of methyl acetoacetate and 358 g (4.16 moles) of 2-methyl- 3-buten-2-ol is added uniformly to the solution obtained. The methanol formed is distilled off continuously.

When the evolution of methanol and $CO_2$ has ceased, the reaction mixture is worked up by distillation. 79 g of unconverted 2-methyl-3-buten-2-ol are recovered and 451 g of 2-methyl-2-hepten-6-one are obtained. The yield of 2-methyl-2-hepten-6-one is 89.5%, based on methyl acetoacetate, and 87.8%, based on 2-methyl-3-buten-2-ol.

COMPARATIVE EXAMPLE (a) 464 g of methyl acetoacetate and 10 g of aluminum triisopropylate are heated to 170° C. in a stirred vessel fitted with a distillation column, and 430 g of 2-methyl-3-buten-2-ol are introduced in the course of 6 hours.

At the top of the column, 253 g of a distillate containing 130 g of methanol, 39 g of acetone, 17 g of isoprene and 60 g of 2-methyl-3-buten-2-ol are obtained during the addition. When the addition is complete, the reaction mixture is heated for a further 2 hours, until the evolution of carbon dioxide ceases.

On fractionally distilling the reaction mixture, 325 g of 2-methyl-2-hepten-6-one and 50 g of 2-methyl-3-buten-2-ol are obtained. The yield is 64% based on alkyl acetoacetate and 67.9% based on 2-methyl-3-buten-2-ol converted (327 g).

During the reaction, the composition of the reaction mixture is as shown in the Table (analysis by gas chromatography: OV17 column material, temperature 100° C., followed by 130° C.).

| After hours reaction time | 2-Methyl-3-buten-2-ol, % | Methyl acetoacetate % | 2-Methyl-2-hepten-6-one, % | Methylbutenol acetoacetate % | Prenyl acetoacetate % |
|---|---|---|---|---|---|
| 1 | 7.0 | 78.3 | 12.5 | 2.1 | — |
| 2 | 6.2 | 52.6 | 30.0 | 2.5 | — |
| 3 | 5.8 | 32.5 | 61.2 | 1.4 | — |
| 4 | 11.0 | 23.1 | 63.2 | 2.1 | — |
| 6 | 15.6 | 10.7 | 72.3 | 2.5 | — |
| 8 | 8.7 | 0 | 90.0 | 0 | — |

(b) 464 g of methyl acetoacetate are heated to 155° C. in a stirred vessel fitted with a distillation column, and 430 g of 2-methyl-3-buten-2-ol are introduced in the course of 6 hours.

On fractional distillation of the reaction mixture, 64 g of unconverted 2-methyl-3-buten-2-ol, 351 g of 2-methyl-2-hepten-6-one and 41 g of prenyl acetoacetate are obtained. The yield is 69.7% of theory, based on alkyl acetoacetate converted, and 65.7% of theory, based on methylbutenol converted.

During the reaction, the composition of the reaction mixture, in % by weight, is as shown in the Table (analysis by gas chromatography: OV17 column material, temperature 100° C., followed by 130° C.).

| After hours reaction time | 2-Methyl-3-buten-2-ol, % | Methyl acetoacetate % | 2-Methyl-2-hepten-6-one, % | Methylbutenol acetoacetate % | Prenyl acetoacetate % |
|---|---|---|---|---|---|
| 1 | 11.1 | 68.6 | 13.9 | 5.3 | 0 |
| 2 | 9.5 | 56.4 | 26.5 | 7.2 | 1.9 |
| 3 | 7.1 | 42.3 | 39.9 | 7.6 | 2.4 |
| 4 | 7.9 | 29.1 | 51.3 | 6.7 | 4.3 |
| 5 | 9.6 | 22.6 | 59.7 | 4.6 | 3.1 |
| 6 | 9.1 | 15.8 | 62.8 | 6.0 | 5.2 |
| 8 | 6.9 | 7.6 | 74.3 | 3.8 | 6.5 |
| end | 7.0 | 0 | 87.1 | 0 | 5.9 |

We claim:
1. In a process for the manufacture of 2-methyl-2-hepten-6-one by reacting 2-methyl-3-buten-2-ol with an alkyl acetoacetate at an elevated temperature in the presence of an organic aluminum compound, the improvement wherein the methylbutenol and the alkyl acetoacetate are reacted at from 140° to 180° C., in a molar ratio of from 0.8:1 to 2.0:1, with the proviso that the concentration of said alkyl acetoacetate in the reaction mixture during the entire reaction period is not above 15% by weight for a total time of more than two hours and wherein said organic aluminum compound has the formula

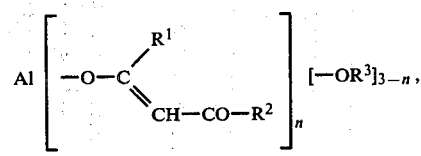

where $R^1$ and $R^2$ are alkyl or alkoxy of 1 to 4 carbon atoms, $R^3$ is alkyl of 1 to 4 carbon atoms and n is 0, 1, 2 or 3 or said aluminum compound is an aluminum triaryloxylate wherein the aryloxy group is phenolate, optionally substituted by lower alkyl or lower alkoxy of 1 to 4 carbon atoms or is naphtholate, optionally substituted by alkyl or alkoxy of 1 to 4 carbon atoms.

2. A process as claimed in claim 1, wherein the methylbutenol and the alkyl acetoacetate are reacted in a molar ratio of from 1:1 to 1.5:1.

3. A process as claimed in claim 1, wherein the methylbutenol and the alkyl acetoacetate are introduced into a solution of the aluminum compound in 2-methyl-2-hepten-6-one.

4. A process as claimed in claim 1, wherein said aluminum triaryloxylate is used as the organic aluminum compound.

5. A process as claimed in claim 4, wherein aluminum triphenolate is used as the organic aluminum compound.

6. A process as claimed in claim 1, wherein the alkylacetoacetate is methyl or ethyl acetoacetate.

7. A process as claimed in claim 1 wherein the concentration of said alkyl acetoacetate in the reaction mixture during the entire reaction period is not above 15% by weight for a total time of more than one hour.

8. A process as claimed in claim 1 wherein the concentration of said alkyl acetoacetate in the reaction mixture never exceeds 5% by weight.

* * * * *